United States Patent
Sugiura et al.

(10) Patent No.: US 6,784,426 B2
(45) Date of Patent: Aug. 31, 2004

(54) ELECTRON BEAM IRRADIATION APPARATUS, ELECTRON BEAM EXPOSURE APPARATUS, AND DEFECT DETECTION METHOD

(75) Inventors: Takayuki Sugiura, Tokyo (JP); Hideki Nasuno, Tokyo (JP)

(73) Assignee: Advantest Corp., Tokyo (JP)

( * ) Notice: Subject to any disclaimer, the term of this patent is extended or adjusted under 35 U.S.C. 154(b) by 0 days.

(21) Appl. No.: 10/686,792

(22) Filed: Oct. 16, 2003

(65) Prior Publication Data

US 2004/0079883 A1 Apr. 29, 2004

(30) Foreign Application Priority Data

Oct. 28, 2002 (JP) ........................... 2002-313428

(51) Int. Cl.[7] ............... H01J 37/28; G01N 23/203
(52) U.S. Cl. ............. 250/310; 250/306; 250/307; 250/396 R; 250/397; 250/398; 250/399; 250/492.1; 250/492.2; 250/492.3
(58) Field of Search ..................... 250/306, 307, 250/310, 396 R, 397–399, 492.1–492.3

(56) References Cited

U.S. PATENT DOCUMENTS

| | | | | |
|---|---|---|---|---|
| 5,430,292 A | * | 7/1995 | Honjo et al. | 250/310 |
| 5,557,105 A | * | 9/1996 | Honjo et al. | 250/310 |
| 5,824,441 A | * | 10/1998 | Farrow et al. | 430/22 |
| 6,541,779 B2 | * | 4/2003 | Fujiwara | 250/491.1 |
| 6,545,274 B1 | * | 4/2003 | Morita | 250/307 |
| 6,627,903 B1 | * | 9/2003 | Hirayanagi | 250/491.1 |
| 2002/0145113 A1 | * | 10/2002 | Sullivan et al. | 250/311 |
| 2004/0079883 A1 | * | 4/2004 | Sugiura et al. | 250/310 |

* cited by examiner

*Primary Examiner*—John R. Lee
*Assistant Examiner*—Bernard Souw
(74) *Attorney, Agent, or Firm*—Muramatsu & Associates

(57) ABSTRACT

An electron beam irradiation apparatus which irradiates an electron beam to an object for easily detecting a defect of a backscattered electron detector, including: an electron beam generating section for generating an electron beam; a plurality of backscattered electron detectors for detecting backscattered electrons generated when the electron beam is irradiated on a mark; a plurality of attenuation sections for attenuating signal values indicating quantity of backscattered electrons detected by the plurality of backscattered electron detectors; and a defect detecting section for detecting a defect of the plurality of backscattered electron detectors based on the signal values attenuated by the plurality of attenuation sections, with attenuation factors for the plurality of attenuation sections being varied.

17 Claims, 5 Drawing Sheets

ELECTRON BEAM IRRADIATION APPARATUS, ELECTRON BEAM EXPOSURE APPARATUS, AND DEFECT DETECTION METHOD

This patent application claims priority on a Japanese patent application, 2002-313428 filed on Oct. 28, 2002, the contents of which are incorporated herein by reference.

BACKGROUND OF THE INVENTION

1. Field of the Invention

The present invention relates to an electron beam irradiation apparatus, an electron beam exposure apparatus, and a defect detection method. More particularly, the present invention relates to an electron beam irradiation apparatus, an electron beam exposure apparatus, and a defect detection method for detecting a defect of a backscattered electron detector.

2. Description of the Related Art

An electron beam exposure apparatus includes a backscattered electron detector for detecting backscattered electrons scattering when an electron beam is irradiated to a mark on a wafer or a wafer stage. The electron beam exposure apparatus performs calibration of the irradiation position of the electron beam, measurement of pattern width written on the wafer, etc. based on quantity of the backscattered electrons detected by the backscattered electron detector. In the conventional electron beam exposure apparatus, the backscattered electron detector is directly connected to a testing apparatus at the time of the assembly of a body tube for checking acceptability of the backscattered electron detector.

Since the backscattered electron detector is assembled in the body tube with an electron lens and a deflector under subatmospheric pressure, it is difficult to perform periodical test of the detector frequently by the conventional method of directly connecting the testing device. Furthermore, since a skilled labor is needed for performing the test, it is less efficient and a number of processes are also required. Moreover, the electron beam exposure apparatus usually includes a plurality of backscattered electron detectors, and even if one backscattered electron detector fails, the other backscattered electron detectors detect a certain amount of backscattered electrons. Therefore, there is a possibility that a user does not notice the failure of the backscattered electron detector, and continues to use it in the state where the quantity of backscattered electrons is not correctly detectable.

SUMMARY OF THE INVENTION

Therefore, it is an object of the present invention to provide an electron beam irradiation apparatus, an electron beam exposure apparatus, and a defect detection method which can solve the foregoing problem. The above and other objects can be achieved by combinations described in the independent claims. The dependent claims define further advantageous and exemplary combinations of the present invention.

According to a first aspect of the present invention, there is provided an electron beam irradiation apparatus for irradiating an electron beam to an object. The electron beam irradiation apparatus includes: an electron beam generating section for generating an electron beam; a plurality of backscattered electron detectors for detecting backscattered electrons generated when the electron beam is irradiated on a mark; a plurality of attenuation sections for attenuating signal values indicating quantity of backscattered electrons detected by the plurality of backscattered electron detectors; and a defect detecting section for detecting a defect of the plurality of backscattered electron detectors based on the signal values attenuated by the plurality of attenuation sections, with attenuation factors for the plurality of attenuation sections being varied.

The electron beam irradiation apparatus may further include: a plurality of IV converters for converting the quantity of electrons detected by the plurality of backscattered electron detectors in to voltages, and for generating signal values indicating the quantity of the backscattered electrons; and a plurality of amplifiers for amplifying the signal values generated by the plurality of IV converters. The defect detecting section may detect a defect of the plurality of backscattered electron detectors, the plurality of IV converters, and the plurality of amplifiers.

The electron beam irradiation apparatus may further include an ideal value storage section storing thereon an ideal value, which is a signal value indicating the quantity of the backscattered electrons detected by the plurality of backscattered electron detectors when the plurality of backscattered electron detectors are normal. The defect detecting section may detect the defect of the plurality of backscattered electron detectors by comparing the signal values attenuated by the plurality of the attenuation sections with the ideal value stored on the ideal value storage section.

The electron beam irradiation apparatus may further include an attenuated signal adder for adding a signal value attenuated by a first attenuation section of the plurality of attenuation sections, and a signal value attenuated by a second attenuation section of the plurality of attenuation sections. The first attenuation section may attenuate the signal value indicating the quantity of the backscattered electrons detected by a first backscattered electron detector of the plurality of backscattered electron detectors by a first attenuation factor based on control of the defect detecting section. The second attenuation section may attenuate the signal value indicating the quantity of the backscattered electrons detected by a second backscattered electron detector of the plurality of backscattered electron detectors by a second attenuation factor based on control of the defect detecting section. The attenuated signal adder may add the signal value attenuated by the first attenuation section by the first attenuation factor, and the signal value attenuated by the second attenuation section by the second attenuation factor, and supplies the added signal to the defect detecting section. The defect detecting section may detect the defect of at least one of the first backscattered electron detector and the second backscattered electron detector by varying the first attenuation factor and the second attenuation factor.

The electron beam irradiation apparatus may further include: a plurality of detected signal adders for adding signal values indicating the quantity of the backscattered electrons detected by the plurality of backscattered electron detectors; and an attenuated signal adder for adding a signal value attenuated by a first attenuation section of the plurality of attenuation sections, and a signal value attenuated by a second attenuation section of the plurality of attenuation sections. The plurality of backscattered electron detectors may include: a first backscattered electron detector and a second backscattered electron detector disposed across an optical axis of the electron beam; and a third backscattered electron detector and a fourth backscattered electron detector disposed across the optical axis of the electron beam. The plurality of detected signal adders may include: a first detected signal adder for adding a signal value indicating the quantity of the backscattered electrons detected by the first backscattered electron detector, and a signal value indicating the quantity of the backscattered electrons detected by the second backscattered electron detector; and a second detected signal adder for adding a signal value indicating the quantity of the backscattered electrons detected by the third backscattered electron detector, and a signal value indicating the quantity of the backscattered electrons detected by the fourth backscattered electron detector. The plurality of attenuation sections may include: a first attenuation section for attenuating a signal value added by the first detected signal adder by a first attenuation factor; and a second attenuation section for attenuating a signal value added by the second detected signal adder by a second attenuation factor. The attenuated signal adder may add the signal value attenuated by the first attenuation section by the first attenuation factor, and the signal value attenuated by the second attenuation section by the second attenuation factor, and supplies the added signal to the defect detecting section. The defect detecting section may detect defect of at least one of the first backscattered electron detector, the second backscattered electron detector, the third backscattered electron detector, and the fourth backscattered electron detector by varying the first attenuation factor and the second attenuation factor.

The electron beam irradiation apparatus may further include: an ideal value storage section storing thereon an ideal value which is a signal value to be supplied from the attenuated signal adder to the defect detecting section when the first backscattered electron detector, the second backscattered electron detector, the third backscattered electron detector, and the fourth backscattered electron detector are normal and when each of the first attenuation factor and the second attenuation factor is set to a predetermined attenuation factor; and a permissible value storage section storing thereon a predetermined permissible value used as a judgment criterion of defect detection. The defect detecting section may judge whether a difference between a first detected signal value, which is a signal value supplied from the attenuated signal adder when each of the first attenuation factor and the second attenuation factor is set to the predetermined attenuation factor, and the ideal value stored on the ideal value storage section is within the predetermined permissible value, and the defect detecting section may detect that at least two of the first backscattered electron detector, the second backscattered electron detector, the third backscattered electron detector, and the fourth backscattered electron detector are defective when it is measured that the difference between the first detected signal value and the ideal value is not within the predetermined permissible value.

The permissible value storage section may further store another permissible value, which is smaller than the predetermined permissible value. The defect detecting section may judge whether each of a difference between the second detected signal value and the half of the first detected signal value, and a difference between the third detected signal value and the half of the first detected signal value, is within the other permissible value when it is measured that the difference between the first detected signal value and the ideal value is within the predetermined permissible value, and the defect detecting section may detect that the first backscattered electron detector, the second backscattered electron detector, the third backscattered electron detector, and the fourth backscattered electron detector are normal when it is judged that each of the difference between the second detected signal value and the half of the first detected signal value, and the difference between the third detected signal value and the half of the first detected signal value, is within the other permissible value. Where the second detected signal value is a signal value supplied from the attenuated signal adder when the first attenuation factor is set to the predetermined attenuation factor and the second attenuation factor is set to another attenuation factor, which is greater than the predetermined attenuation factor, and the third detected signal value is a signal value supplied from the attenuated signal adder when the first attenuation factor is set to the other attenuation factor and the second attenuation factor is set to the predetermined attenuation factor.

The defect detecting section may compare the second detected signal value with the third detected signal value when it is measured that either the difference between the second detected signal value and the half of the first detected signal value, or the difference between the third detected signal value and the half of the first detected signal value, is not within the other permissible value, and the defect detecting section may detect that at least one of the first backscattered electron detector and the second backscattered electron detectors is defective when the second detected signal value is less than the third detected signal value, and the defect detecting section detects that at least one of the third backscattered electron detector or the fourth backscattered electron detectors is defective when the third detected signal value is less than the second detected signal value.

According to a second aspect of the present invention, there is provided a defect detection method of detecting a defect of a backscattered electron detector. The defect detection method includes steps of: detecting backscattered electrons by a plurality of backscattered electron detectors, the backscattered electrons being generated when an electron beam is irradiated on the mark; attenuating signal values indicating quantity of backscattered electrons detected by the plurality of backscattered electron detectors; and detecting a defect of the plurality of backscattered electron detectors based on attenuated signal values, with attenuation factors in the attenuation step being varied.

The defect detection step may include a step of detecting defect of the plurality of backscattered electron detectors by comparing the ideal value, which is a signal value indicating the quantity of the backscattered electrons detected by the plurality of backscattered electron detectors when the plurality of backscattered electron detectors are normal, with the signal value attenuated in the attenuation step.

The attenuation step may include steps of: attenuating a signal value indicating the quantity of the backscattered electrons detected by a first backscattered electron detector of the plurality of backscattered electron detectors by a first attenuation factor; and attenuating a signal value indicating the quantity of the backscattered electrons detected by a second backscattered electron detector of the plurality of backscattered electron detectors by a second attenuation factor. A defect of at least one of the first backscattered electron detector and the second backscattered electron detector may be detected in the defect detection step based on a signal value, which is a summation of the signal value attenuated by the first attenuation factor and the signal value attenuated by the second attenuation factor in the attenuation steps by varying the first attenuation factor and the second attenuation factor.

The backscattered electron detection step may include a step of detecting the backscattered electrons by a first backscattered electron detector and a second backscattered electron detector disposed across an optical axis of the electron beam, and by a third backscattered electron detector and a fourth backscattered electron detector disposed across an optical axis of the electron beam. The attenuation step may include steps of: generating a first attenuation signal value by attenuating the signal value, which is a summation of the signal value indicating the quantity of backscattered electrons detected by the first backscattered electron detector and the signal value indicating the quantity of backscattered electrons detected by the second backscattered electron detector, by a first attenuation factor; and generating a second attenuation signal value by attenuating the signal value, which is a summation of the signal value indicating the quantity of backscattered electrons detected by the third backscattered electron detector and the signal value indicating the quantity of backscattered electrons detected by the fourth backscattered electron detector, by a second attenuation factor. A defect of at least one of the first backscattered electron detector, the second backscattered electron detector, the third backscattered electron detector, and the fourth backscattered electron detector may be detected in the defect detection step based on the signal value, which is a summation of the first attenuation signal value and the second attenuation signal value generated in the attenuation step, by varying the first attenuation factor and the second attenuation factor.

The defect detection step may include steps of: judging whether difference between a first detected signal value and an ideal value is within a predetermined permissible value; and detecting that at least two of the first backscattered electron detector, the second backscattered electron detector, the third backscattered electron detector, and the fourth backscattered electron detectors are defective when it is measured that the difference between the first detected signal value and the ideal value is not within the predetermined permissible value. Where, the first detected signal value is a summation of the first attenuation signal value and the second attenuation signal value where each of the first attenuation factor and the second attenuation factor is set to a predetermined attenuation factor, and the ideal value is a summation of the first attenuation signal value and the second attenuation signal value when the first backscattered electron detector, the second backscattered electron detector, the third backscattered electron detector, and the fourth backscattered electron detector are normal and each of the first attenuation factor and the second attenuation factor is set to the predetermined attenuation factor.

The defect detection step may include steps of: judging whether each of a difference between a second detected signal value and the half of the first detected signal value, and a difference between a third detected signal value and the half of the first detected signal value, is within another permissible value, which is smaller than the predetermined permissible value, when it is measured that the difference between the first detected signal value and the ideal value is within the predetermined permissible value; and detecting that the first backscattered electron detector, the second backscattered electron detector, the third backscattered electron detector, and the fourth backscattered electron detector are normal when it is judged that each of the difference between the second detected signal value and the half of the first detected signal value, and the difference between the third detected signal value and the half of the first detected signal value, is within the other permissible value. Where, the second detected signal value is a summation of the first attenuation signal value and the second attenuation signal value when the first attenuation factor is set to the predetermined attenuation factor and the second attenuation factor is set to another attenuation factor, which is greater than the predetermined attenuation factor, and the third detected signal is a summation of the first attenuation signal value and the second attenuation signal value when the first attenuation factor is set to the other attenuation factor and the second attenuation factor is set to the predetermined attenuation factor.

The defect detection method may further include a step of storing the first detected signal value as the ideal value when it is detected in the defect detection step that the first backscattered electron detector, the second backscattered electron detector, the third backscattered electron detector, and the fourth backscattered electron detector are normal.

The defect detection step may include steps of: comparing the second detected signal value with the third detected signal value when at least either the difference between the second detected signal value and the half of the first detected signal value, or the difference between the third detected signal value and the half of the first detected signal value, is not within the other permissible value; and detecting that at least one of the first backscattered electron detector and the second backscattered electron detector is defective when the second detected signal value is less than the third detected signal value, and detecting that at least one of the third backscattered electron detector and the fourth backscattered electron detector is defective when the third detected signal value is less than the second detected signal value.

According to a first aspect of the present invention, there is provided an electron beam exposure apparatus for exposing a pattern on a wafer by an electron beam. The electron beam exposure apparatus includes: an electron beam generating section for generating an electron beam; a plurality of backscattered electron detectors for detecting backscattered electrons generated when the electron beam is irradiated on a mark; a plurality of attenuation sections for attenuating signal values indicating quantity of backscattered electrons detected by the plurality of backscattered electron detectors; and a defect detecting section for detecting a defect of the plurality of backscattered electron detectors by varying attenuation factors for the plurality of attenuation sections.

The summary of the invention does not necessarily describe all necessary features of the present invention. The present invention may also be a sub-combination of the features described above.

DETAILED DESCRIPTION OF THE INVENTION

The invention will now be described based on the preferred embodiments, which do not intend to limit the scope of the present invention, but exemplify the invention. All of the features and the combinations thereof described in the embodiment are not necessarily essential to the invention.

Figure 1:
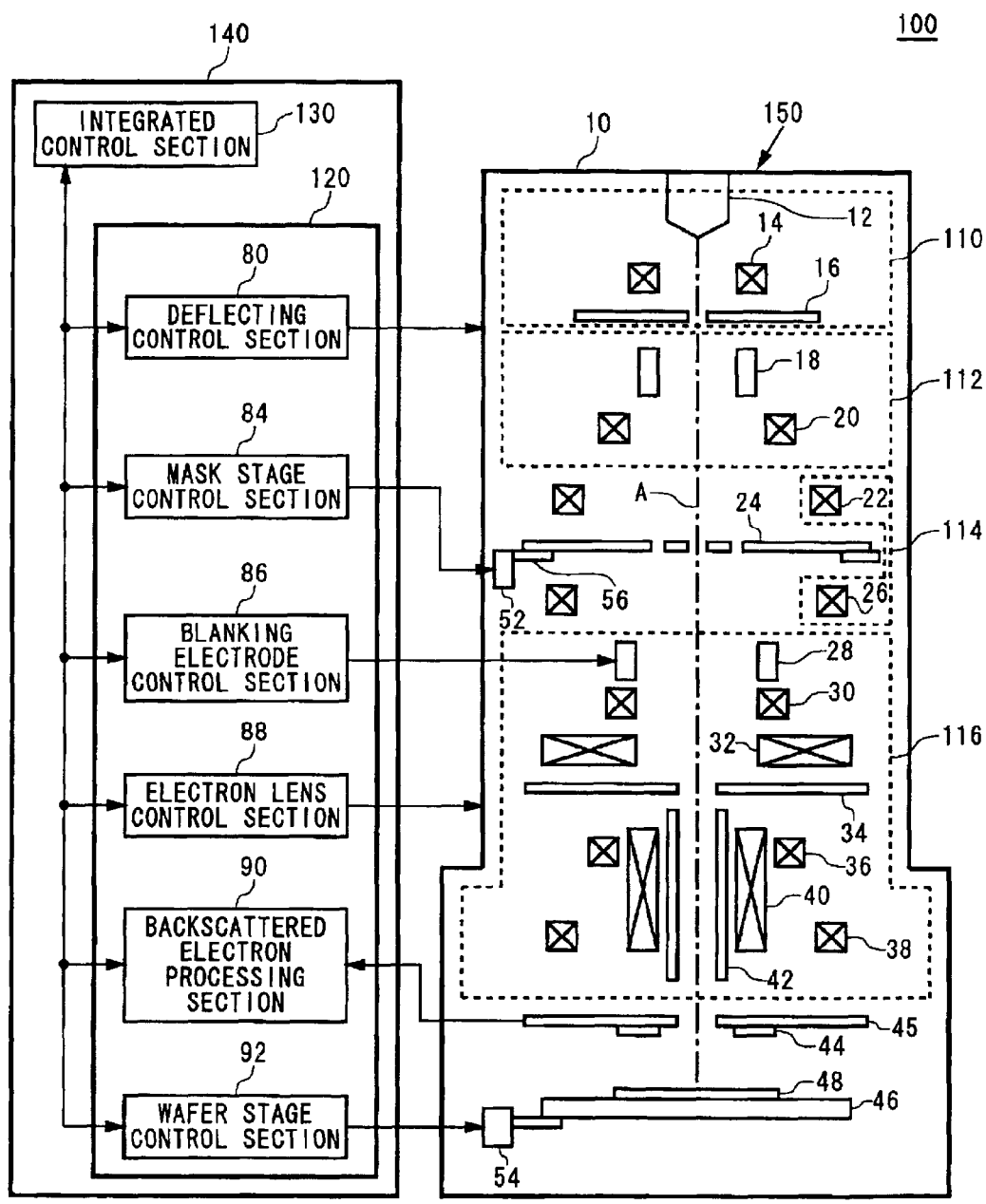
FIG. 1 is a schematic view of a configuration of an electron beam exposure apparatus.

FIG. 1 is a block diagram of an electron beam exposure apparatus 100 according to an embodiment of the present invention. The electron beam exposure apparatus 100 includes an exposure section 150 for performing predetermined exposure processing on a wafer 48 by an electron beam, and a control system 140 for controlling operation of components of the exposure section 150.

The exposure section 150 includes an electron optics system, which includes: an electron beam discharge system 110 for discharging a predetermined electron beam into a body tube 10; a mask projection system 112 for deflecting the electron beam discharged from the electron beam discharge system 110 and for adjusting a focal point of the electron beam in the vicinity of a mask 24; a focal point adjustment lens system 114 for adjusting a focal point of the electron beam, which has passed through the mask 24, in the vicinity of the wafer 48; and a wafer projection system 116 for deflecting the electron beam, which has passed through the mask 24, to a predetermined area of the wafer 48 mounted on a wafer stage 46, and for adjusting a direction and a size of an image of a pattern which is to be written to the wafer 48.

Moreover, the exposure section 150 includes: a mask 24 including a plurality of aperture patterns, each of which is shaped into a shape which is to be exposed on the wafer 48; a mask stage 56 on which the mask 24 is mounted; a mask stage drive section 52 for driving the mask stage 56; a wafer stage 46 on which the wafer 48 is mounted; a wafer stage drive section 54 for driving the wafer stage 46; and an electron detecting section 45 including a plurality of backscattered electron detectors 44 for detecting electrons scattered from a direction of the wafer stage 46 and converting the quantity of the scattered electrons into corresponding electrical signal. For example, the backscattered electron detectors 44 are pin diodes.

The electron beam discharge system 110 includes: an electron gun 12, which is an example of an electron beam generating section for generating an electron beam; a first electron lens 14 for focusing the electron beam discharged from the electron gun 12; and a slit section 16 with an aperture (slit) having a rectangle shape through which the electron beam passes. An alternate long and short dash line A in FIG. 1 indicates an optical axis of the electron beam discharged from the electron beam discharge system 110 when the electron beam is not deflected by the electron optics system.

The mask projection system 112 includes: a deflector 18 as a deflecting system for the mask for deflecting the electron beam; and a second electron lens 20 as a focus system for the mask for adjusting a focal point of the electron beam. The deflector 18 deflects the electron beam to a direction substantially perpendicular to the mask 24 and to a predetermined area on the mask 24. The second electron lens 20 has a function for focusing the pattern of the aperture of the slit section 16 onto the mask 24. The focal point adjustment lens system 114 includes a third electron lens 22 and a fourth electron lens 26. The third electron lens 22 and the fourth electron lens 26 adjust the focusing condition of the electron beam before and after the electron beam passes through the mask 24.

The wafer projection system 116 includes a fifth electron lens 30, a sixth electron lens 32, a seventh electron lens 36, an eighth electron lens 38, a main deflector 40, a sub deflector 42, a blanking electrode 28, and a round aperture section 34. The fifth electron lens 30 adjusts the rotation of the pattern image of the electron beam which has passed through a predetermined aperture pattern in the mask 24. The sixth electron lens 32 and the seventh electron lens 36 adjust the reduction ratio of the pattern image exposed on the wafer 48 to the aperture pattern formed in the mask 24. The eighth electron lens 38 functions as an objective lens. The main deflector 40 and the sub deflector 42 deflect the electron beam so that the electron beam is applied on a predetermined area of the wafer 48.

The round aperture section 34 includes a circular aperture (round aperture). The blanking electrode 28 prevents the electron beam going to the downstream of the round aperture section 34 by deflecting the electron beam so that it hits outside of the round aperture. Since the electron gun 12 continuously discharges the electron beam during the period of the exposure processing, it is preferable that the blanking electrode 28 deflects the electron beam so that the electron beam may not go to downstream of the round aperture section 34 when changing the pattern to be exposed on the wafer 48, or when changing areas in the wafer 48 on which the pattern is to be exposed.

The control system 140 includes an integrated control section 130 and an individual control section 120. The individual control section 120 includes a deflecting control section 80, a mask stage control section 84, a blanking electrode control section 86, an electron lens control section 88, a backscattered electron processing section 90, and a wafer stage control section 92.

The deflecting control section 80 controls the deflector 18, the main deflector 40, and the sub deflector 42. The mask stage control section 84 controls the mask stage drive section 52, and causes the mask stage drive section 52 to move the mask stage 56. The blanking electrode control section 86 controls the blanking electrode 28 so that the electron beam is applied on the wafer 48 when the wafer is being exposed, and causes the blanking electrode 28 to deflects the electron beam so that the electron beam may not go to downstream of the round aperture section 34 when the wafer 48 is not being exposed. The electron lens control section 88 controls electric power supplied to the first electron lens 14, the second electron lens 20, the third electron lens 22, the fourth electron lens 26, the fifth electron lens 30, the sixth electron lens 32, the seventh electron lens 36, and the eighth electron lens 38. The backscattered electron processing section 90 amplifies electric signal output from the backscattered electron detectors 44, and supplies it to the integrated control section 130. The wafer stage control section 92 causes the wafer stage drive section 54 to move the wafer stage 46 to a predetermined position.

For example, the integrated control section 130 is a work station and collectively controls each of the control sections of the individual control section 120. Moreover, the integrated control section 130 detects a defect of the backscattered electron detectors 44 based on the electric signal acquired from the backscattered electron processing section 90.

Alternatively, the electron beam exposure apparatus 100 is a variable rectangle exposure apparatus for writing a pattern to the wafer 48 by a variable rectangle beam, or it is a multi-beam exposure apparatus for writing a pattern to the wafer 48 by a plurality of electron beams. Moreover, the electron beam exposure apparatus 100 is an example of the electron beam irradiation apparatus of the present invention, and the wafer stage 46 and the wafer 48 are a stage and an object of the present invention, respectively. The electron beam irradiation apparatus of the present invention may be an electron microscope, an electron beam tester, etc., instead of the electron beam exposure apparatus.

Figure 2:
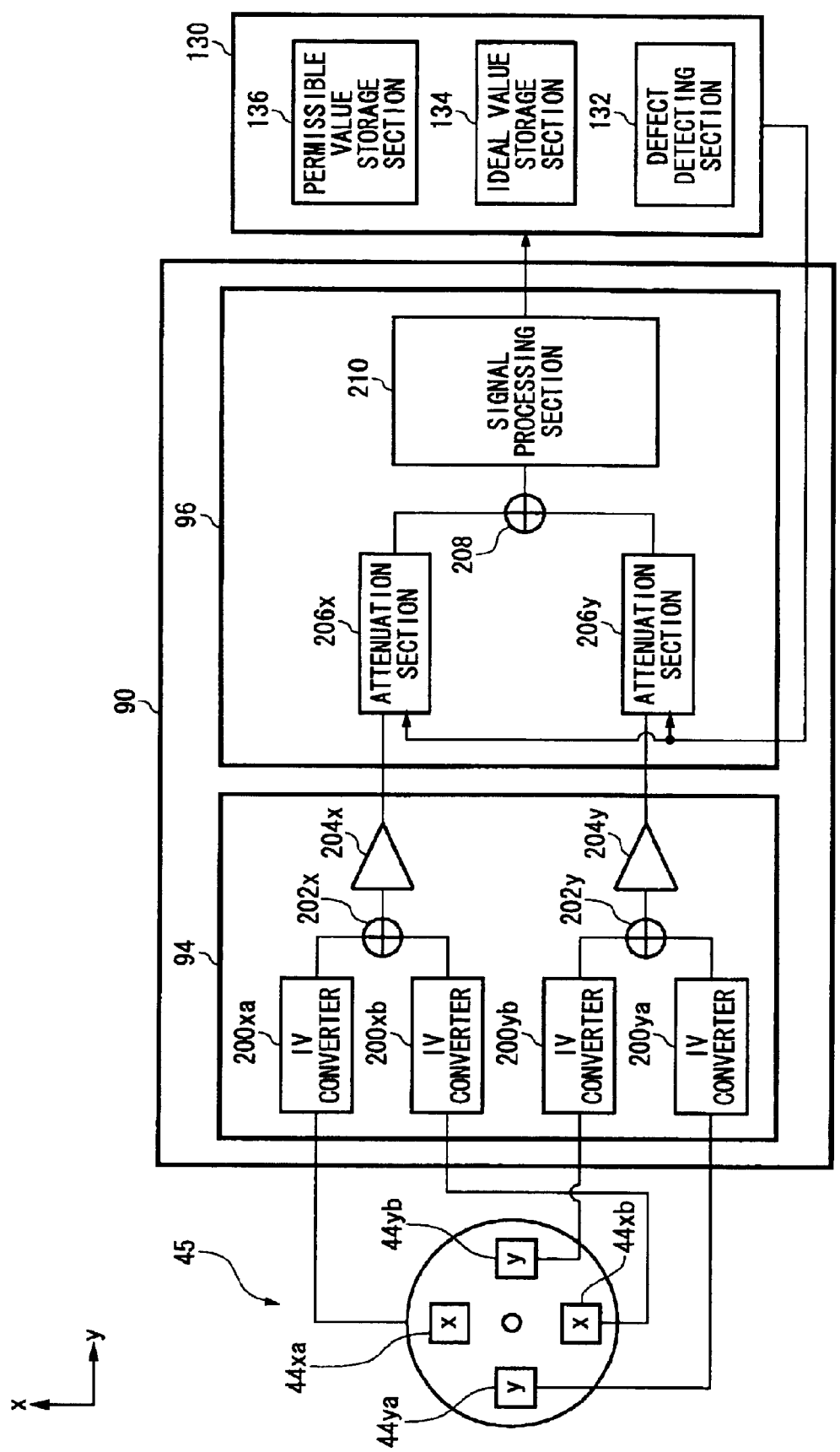
FIG. 2 is a block diagram exemplary showing a configuration of an electron detecting section, a backscattered electron processing section, and an integrated control section.

FIG. 2 is a block diagram exemplary showing a configuration of the electron detecting section 45, the backscattered electron processing section 90, and the integrated control section 130. The electron detecting section 45 includes a plurality of backscattered electron detectors 44xa, 44ya, 44xb, and 44yb. The integrated control section 130 includes a defect detecting section 132, an ideal value storage section 134, and a permissible value storage section 136. The backscattered electron processing section 90 includes a preamplifier section 94 and a video board amplifier section 96. The preamplifier section 94 includes a plurality of IV converters 200xa, 200ya, 200xb, and 200yb, a plurality of adders 202x and 202y, and a plurality of amplifiers 204x and 204y. The adders 202x and 202y are examples of detected signal adders according to the present invention. The video board amplifier section 96 includes a plurality of attenuation sections 206x and 206y, an adder 208, and a signal processing section 210. The adder 208 is an example of the attenuated signal adder according to the present invention. Alternatively, the attenuation sections 206x and 206y are attenuators for attenuating the input signals and outputting them, or amplifiers for amplifying the input signals and outputting them.

The backscattered electron detectors 44xa, 44ya, 44xb, and 44yb detect the backscattered electrons generated when the electron beam is irradiated on a mark formed on the wafer stage 46 or the wafer 48. At this time, in case that the backscattered electron detectors 44xa, 44ya, 44xb, and 44yb are normal, it is preferable that the electron beam is irradiated on the mark so that the quantity of the backscattered electrons detected by each of the backscattered electron detectors 44xa, 44ya, 44xb, and 44yb per unit time is substantially the same as one another. Alternatively, the backscattered electron detectors 44xa, 44ya, 44xb, and 44yb detect the backscattered electrons generated by irradiating the electron beam at substantially the center of the mark.

The backscattered electron detector 44xa and the backscattered electron detector 44xb are oppositely disposed across the optical axis A of the electron beam. The backscattered electron detector 44ya and the backscattered electron detector 44yb are oppositely disposed across the optical axis A of the electron beam. Moreover, it is preferable that a direction from the backscattered electron detector 44xa to the backscattered electron detector 44xb is substantially perpendicular to a direction from the backscattered electron detector 44ya to the backscattered electron detector 44yb. That is, the backscattered electron detectors 44xa and 44xb detect the backscattered electrons scattering in the direction of x-axis in FIG. 2, and the backscattered electron detectors 44ya and 44yb detect the backscattered electrons scattering in the direction of y-axis in FIG. 2.

The plurality of IV converters 200xa, 200xb, 200ya, and 200yb convert the quantity of the electrons detected by the plurality of backscattered electron detectors 44xa, 44xb, 44ya, and 44yb into voltage, and generate signal values indicating the quantity of the detected backscattered electrons, respectively.

The adder 202x acquires the signal values indicating the quantity of the backscattered electrons detected by the plurality of backscattered electron detectors 44xa and 44xb from the IV converters 200xa and 200xb, respectively. Then, the adder 202x adds the signal value indicating the quantity of the backscattered electrons detected by the backscattered electron detector 44xa, and the signal value indicating the quantity of the backscattered electrons detected by the backscattered electron detector 44xb. Moreover, the adder 202y acquires the signal values indicating the quantity of the backscattered electrons detected by the plurality of backscattered electron detectors 44ya and 44yb from the IV converters 200ya and 200yb, respectively. Then, the adder 202y adds the signal value indicating the quantity of the backscattered electrons detected by the backscattered electron detector 44ya, and the signal value indicating the quantity of the backscattered electrons detected by the backscattered electron detector 44yb. That is, the adder 202x generates the signal value indicating the quantity of the backscattered electrons scattering in the direction of x-axis in FIG. 2 among the backscattered electrons generated when the electron beam is irradiated on the mark, and the adder 202y generates the signal value indicating the quantity of the backscattered electrons scattering in the direction of y-axis in FIG. 2 among the backscattered electrons generated when the electron beam is irradiated on the mark.

The plurality of amplifiers 204x and 204y amplify the signal values generated by the IV converters 200xa, 200xb, 200ya, and 200yb. The amplifier 204x amplifies the signal value generated by the adder 202x adding the signal value generated by the IV converter 200xa and the signal value generated by the IV converter 200xb. Moreover, the amplifier 204y amplifies the signal value generated by the adder 202y adding the signal value generated by the IV converter 200ya and the signal value generated by the IV converter 200yb.

The plurality of attenuation sections 206x and 206y attenuate the signal values amplified by the plurality of amplifiers 204x and 204y, respectively. That is, the plurality of attenuation sections 206x and 206y attenuate the signal values indicating the quantity of the backscattered electrons detected by the plurality of backscattered electron detectors 44xa, 44xb, 44ya, and 44yb. The attenuation section 206x attenuates the signal value indicating the quantity of the backscattered electrons detected by at least one of the backscattered electron detectors 44xa and 44xb by a first attenuation factor based on the control of the defect detecting section 132. The attenuation section 206y attenuates the signal value indicating the quantity of the backscattered electrons detected by at least one of the backscattered electron detectors 44ya and 44yb by a second attenuation factor based on the control of the defect detecting section 132.

The adder 208 adds the signal value attenuated by the attenuation section 206x by the first attenuation factor, and the signal value attenuated by the attenuation section 206y by the second attenuation factor, and supplies it to the defect detecting section 132 through the signal processing section 210. The signal processing section 210 performs predetermined signal processing to the signal value acquired from the adder 208. Specifically, the signal processing section 210 includes a gain adjustment section, an offset adjustment section, a noise filter section, etc. The gain adjustment section amplifies the signal output from the attenuation sections 206x and 206y and added by the adder 208 to a desired gain suitable for the shape of the mark. The offset adjustment section adds offset to the signal output from the attenuation sections 206x and 206y and added by the adder 208, and shifts it to a signal suitable for an input signal into the defect detecting section 132. The noise filter restricts the frequency band of the signal output from the attenuation sections 206x and 206y and added by the adder 208, and removes high frequency noise.

The defect detecting section 132 detects the defect of the plurality of backscattered electron detectors 44xa, 44xb, 44ya, and 44yb based on the signal values attenuated by the plurality of attenuation sections 206x and 206y when the attenuation factors for the plurality of attenuation sections 206x and 206y are varying, respectively. The defect detecting section 132 detects the defect of at least one of the plurality of backscattered electron detectors 44xa, 44xb, 44ya, and 44yb by varying the first attenuation factor, which is the attenuation factor for the attenuation section 206x, and the second attenuation factor, which is the attenuation factor for the attenuation section 206y, respectively. Alternatively, the defect detecting section 132 detects the defect of the plurality of IV converters 200xa, 200xb, 200ya and 200yb, or a plurality of amplifiers 204x and 204y based on the signal values attenuated by the plurality of attenuation sections 206x and 206y, respectively.

The ideal value storage section 134 stores an ideal value, which is a signal value indicating the quantity of the backscattered electrons detected by the plurality of backscattered electron detectors 44xa, 44xb, 44ya, and 44yb. Specifically, the ideal value storage section 134 stores the ideal value, which is the signal values to be supplied to the defect detecting section 132 from the adder 208 when the plurality of backscattered electron detectors 44xa, 44xb, 44ya, and 44yb are normal and when each of the first attenuation factor for the attenuation section 206x and the second attenuation section for the attenuation section 206y is a predetermined attenuation factor. The defect detecting section 132 detects the defect of the plurality of backscattered electron detectors 44xa, 44xb, 44ya, and 44yb by comparing the signal attenuated by the plurality of attenuation sections 206x and 206y and added by the adder 208 with the ideal value stored on the ideal value storage section 134.

The permissible value storage section 136 stores the permissible values $\alpha_1$ and $\alpha_2$ used as judgment criteria of the defect detection of the plurality of backscattered electron detector 44xa, 44xb, 44ya, and 44yb. The defect detecting section 132 detects the defect of the plurality of backscattered electron detectors 44xa, 44xb, 44ya, and 44yb based on the ideal value stored on the ideal value storage section 134 and the permissible values stored on the permissible value storage section 136.

Figure 3A:
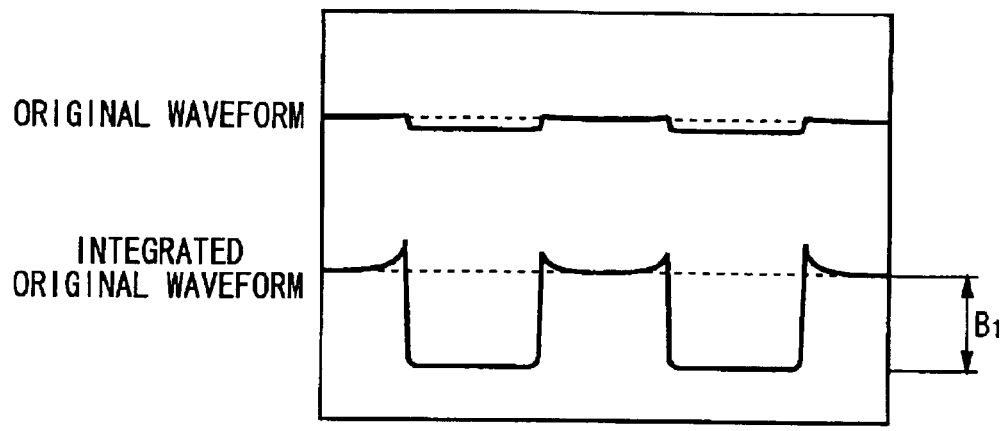
FIGS. 3A to 3C are drawings exemplary showing detection results of a defect detecting section.
Figure 3B:
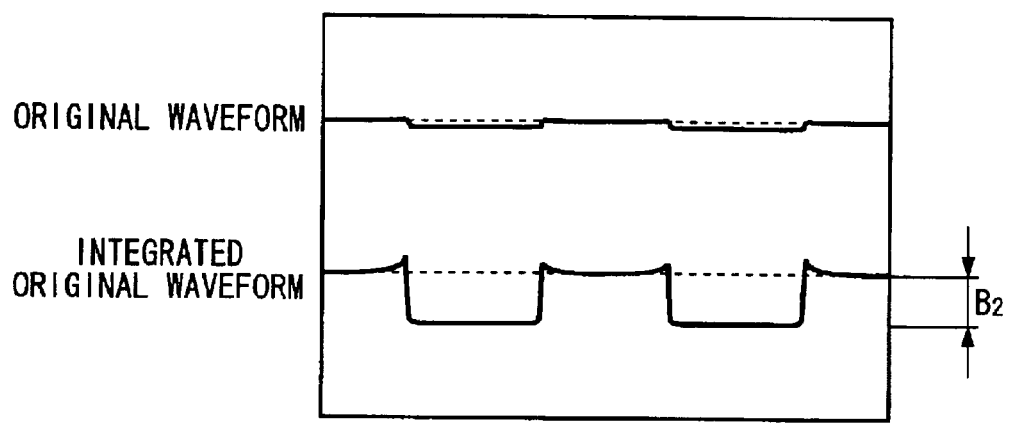
Figure 3C:
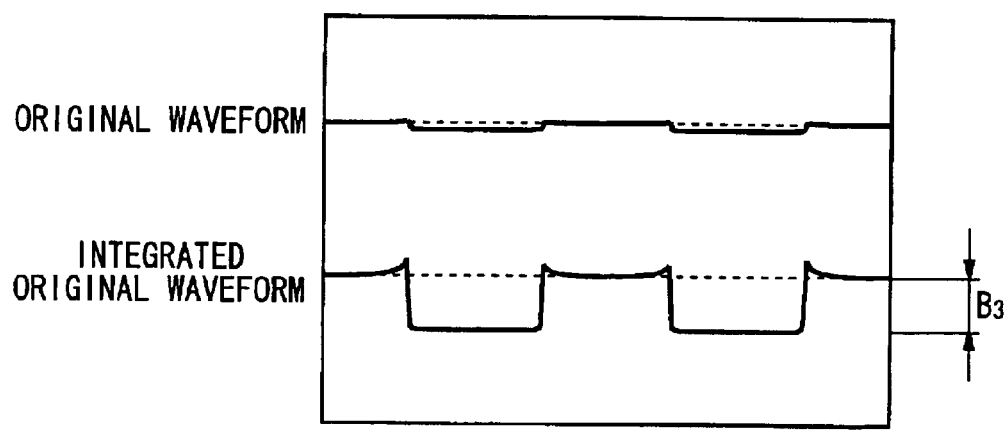
Figure 4A:
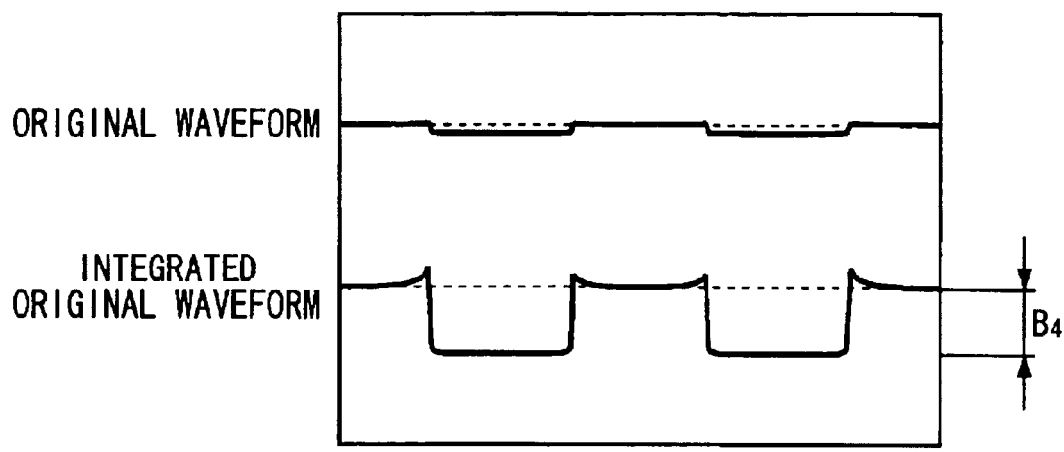
FIGS. 4A to 4C are drawings exemplary showing detection result of the defect detecting section.
Figure 4B:
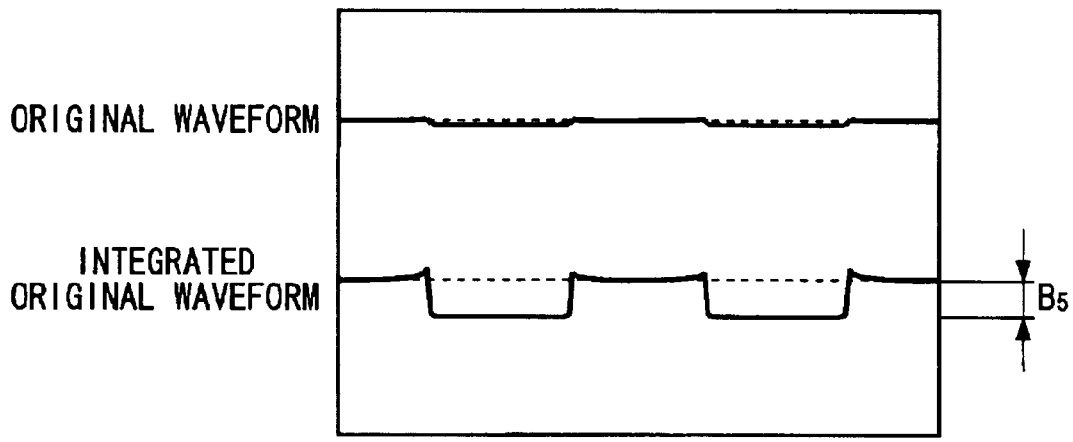
Figure 4C:
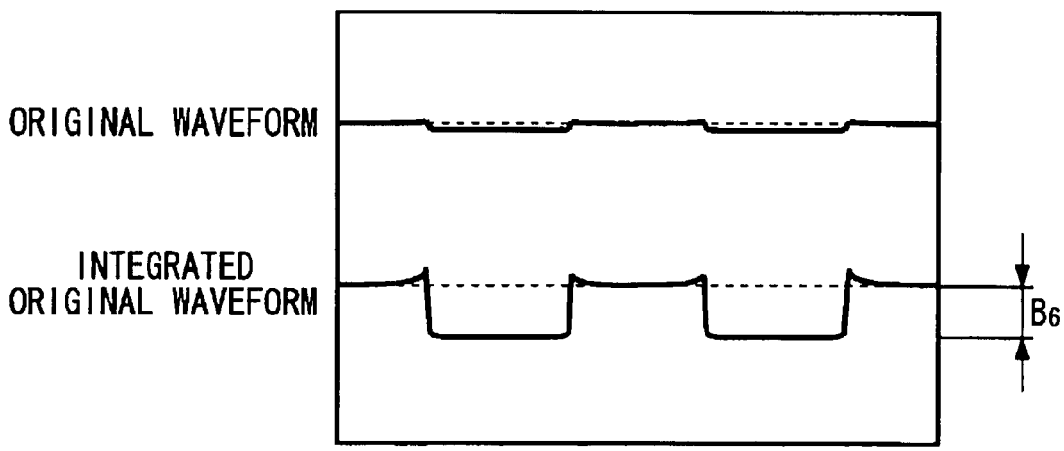

FIGS. 3A, 3B, 3C, 4A, 4B and 4C is drawings exemplary showing the detection results of the defect detecting section 132. FIGS. 3A, 3B and 3C show the signal values acquired by the defect detecting section 132 when the backscattered electron detectors 44xa, 44xb, 44ya, and 44yb are normal. FIGS. 4A, 4B and 4C show the signal values acquired by the defect detecting section 132 when one of the backscattered electron detectors 44xa and 44xb is defective and the other backscattered electron detectors are normal. Moreover, it is postulated that the components other than the defective backscattered electron detector 44xa, 44xb, 44ya, or 44yb shown in FIG. 2 are normal, and also there is no defect in the wiring connecting the components with one another.

The original waveform shown in the upper part of each of FIGS. 3A, 3B, 3C, 4A, 4B and 4C is a waveform of the signal acquired by the defect detecting section 132, and the integrated original waveform shown in the lower part of each of FIGS. 3A, 3B, 3C, 4A, 4B and 4C is a waveform indicating the summation of the original waveforms which are acquired by the defect detecting section 132 for multiple times. Since the amplitude of the original waveform is small, it is preferable that the defect detecting section 132 detects the defect using the amplitude of the signal value of the integrated original waveform. In this example, the integrated original waveform is given by the summation of the original waveforms which are acquired for eight times. In addition, the predetermined attenuation factor may be the greatest attenuation factor for the attenuation sections 206x and 206y, and another attenuation factor may be the minimum attenuation factor for the attenuation sections 206x and 206y, i.e., zero.

FIG. 3A shows the signal value acquired by the defect detecting section 132, where each of the first attenuation factor for the attenuation section 206x and the second attenuation factor for the attenuation section 206y is set to the predetermined attenuation factor. As shown in FIG. 3A, when the backscattered electron detector 44xa, 44xb, 44ya, and 44yb are normal, and when each of the first attenuation factor for the attenuation section 206x and the second attenuation factor for attenuation section 206y is set to the predetermined attenuation factor, the defect detecting section 132 acquires the waveform of the signal value $B_1$.

FIG. 3B shows the signal value acquired by the defect detecting section 132 when the first attenuation factor for the attenuation section 206x is set to the predetermined attenuation factor and the second attenuation factor for the attenuation section 206y is set to the other attenuation factor. As shown in FIG. 3B, when the backscattered electron detector 44xa, 44xb, 44ya, and 44yb are normal, and when the first attenuation factor is set to the predetermined attenuation factor and the second attenuation factor is set to the other attenuation factor, the defect detecting section 132 acquires the waveform of the signal value $B_2$. The signal value $B_2$ is about half of the signal value $B_1$ shown in FIG. 3A. That is, the attenuation section 206y attenuates the signal value indicating the quantity of the backscattered electrons detected by the backscattered electron detectors 44ya and 44yb, and the defect detecting section 132 acquires the signal value indicating the quantity of backscattered electrons detected by the backscattered electron detectors 44xa and 44xb.

FIG. 3C shows the signal value acquired by the defect detecting section 132 when the first attenuation factor for the attenuation section 206x is set to the other attenuation factor and the second attenuation factor for the attenuation section 206y is set to the predetermined attenuation factor. As shown in FIG. 3C, when the backscattered electron detector 44xa, 44xb, 44ya, and 44yb are normal, and when the first attenuation factor is set to the other attenuation factor and the second attenuation factor is set to the predetermined attenuation factor, the defect detecting section 132 acquires the waveform of the signal value $B_3$. The signal value $B_3$ is about half of the signal value $B_1$ shown in FIG. 3A, i.e., substantially the same as the signal value $B_2$ shown in FIG. 3B. That is, the attenuation section 206x attenuates the signal value indicating the quantity of the backscattered electrons detected by the backscattered electron detectors 44xa and 44xb, and the defect detecting section 132 acquires the signal value indicating the quantity of backscattered electrons detected by the backscattered electron detectors 44ya and 44yb.

FIG. 4A shows the signal value acquired by the defect detecting section 132, where each of the first attenuation factor for the attenuation section 206x and the second attenuation factor for the attenuation section 206y is set to the predetermined attenuation factor. As shown in FIG. 4A, when one of the backscattered electron detectors 44xa and 44xb is defective and the other backscattered electron detectors are normal, and when each of the first attenuation factor for the attenuation section 206x and the second attenuation factor for the attenuation section 206y is set to the predetermined attenuation factor, the defect detecting section 132 acquires the waveform of the signal value $B_4$. The signal value $B_4$ is about three-quarters of the signal value $B_1$ shown in FIG. 3A. That is, since one of the backscattered electron detectors 44xa and 44xb is defective, the defect detecting section 132 acquires the signal value indicating the quantity of backscattered electrons detected by one of the backscattered electron detectors 44xa and 44xb, and by the backscattered electron detectors 44ya and 44yb.

FIG. 4B shows the signal value acquired by the defect detecting section 132, where the first attenuation factor for the attenuation section 206x is set to the predetermined attenuation factor and the second attenuation factor for the attenuation section 206y is set to the other attenuation factor. As shown in FIG. 4B, when one of the backscattered electron detectors 44xa and 44xb is defective and the other backscattered electron detectors are normal, and when the first attenuation factor is set to the predetermined attenuation factor and the second attenuation factor is set to the other attenuation factor, the defect detecting section 132 acquires the waveform of signal value $B_5$. The signal value B5 is about one-third of the signal value $B_4$ shown in FIG. 4A. That is, since one of the backscattered electron detectors 44xa and 44xb is defective, the backscattered electrons are not detected by the defective backscattered electron detector, the attenuation section 206y attenuates the signal value indicating the quantity of backscattered electrons detected by the backscattered electron detectors 44ya and 44yb, and the defect detecting section 132 acquires the signal value indicating the quantity of backscattered electrons detected by one of the backscattered electron detectors 44xa and 44xb, which is normal.

FIG. 4C shows the signal value acquired by the defect detecting section 132, where the first attenuation factor for the attenuation section 206x is set to the other attenuation factor and the second attenuation factor for the attenuation section 206y is set to the predetermined attenuation factor. As shown in FIG. 4C, when one of the backscattered electron detectors 44xa or 44xb is defective and the other backscattered electron detectors are normal, and when the first attenuation factor is set to the other attenuation factor and the second attenuation factor is set to the predetermined attenuation factor, the defect detecting section 132 acquires the waveform of signal value $B_6$. The signal value $B_6$ is about two-thirds of the signal value $B_4$ shown in FIG. 4A, i.e., about twice of the signal value $B_5$ shown in FIG. 4B. That is, since one of the backscattered electron detectors 44xa and 44xb is defective, the backscattered electrons are not detected by the defective backscattered electron detector, the attenuation section 206x attenuates the signal value indicating the quantity of backscattered electrons detected by one of the backscattered electron detectors 44xa and 44xb, which is normal, and the defect detecting section 132 acquires the signal value indicating the quantity of backscattered electrons detected by the backscattered electron detectors 44ya and 44yb.

As shown in FIGS. 3A, 3B, 3C 4A 4B and 4C, the defect detecting section 132 detects the defect of at least one of the backscattered electron detectors 44xa, 44xb, 44ya, and 44yb based on the difference in the signal value acquired when the attenuation factors for the attenuation sections 206x and 206y vary.

Figure 5:
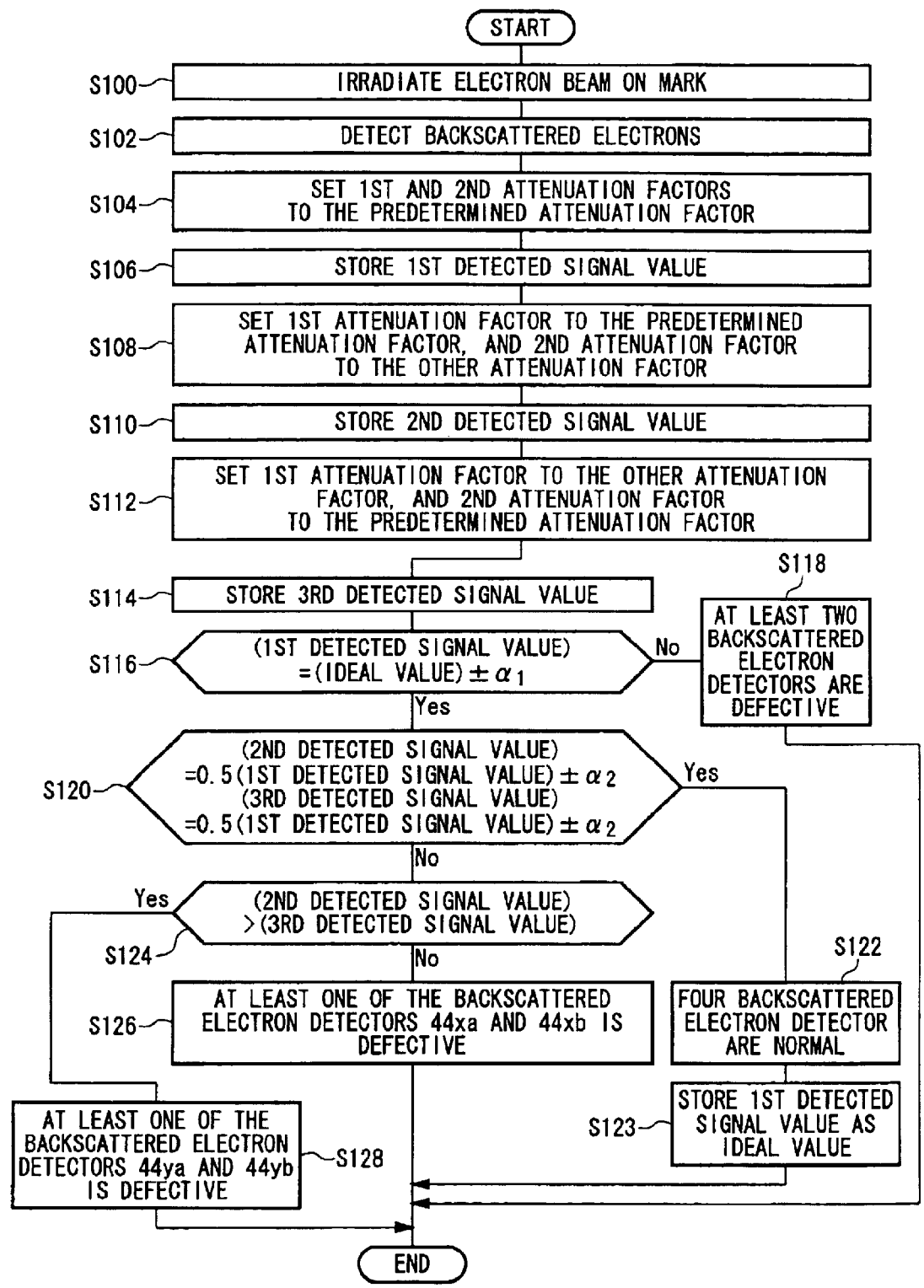
FIG. 5 is a flow chart exemplary showing a flow of a defect detection method of a backscattered electron detector.

FIG. 5 is a flow chart exemplary showing the flow of a detection method of the defective backscattered electron detector. First, the electron beam is irradiated on the mark (S100). Then, the backscattered electron detectors 44xa, 44xb, 44ya, and 44yb detect the backscattered electrons generated when the electron beam is irradiated on the mark (S102).

Next, the defect detecting section 132 sets each of the first attenuation factor and the second attenuation factor to the predetermined attenuation factor (S104). Then, the attenuation section 206x attenuates the signal indicating the quantity of backscattered electrons detected by the backscattered electron detectors 44xa and 44xb by the predetermined attenuation factor, and the attenuation section 206y attenuates the signal indicating the quantity of the backscattered electrons detected by the backscattered electron detectors 44ya and 44yb by the predetermined attenuation factor.

Then, the defect detecting section 132 stores the signal value supplied from the adder 208 through the signal processing section 210 in S104, i.e., a first detected signal value which is a summation of the signal value attenuated by the attenuation section 206x by the predetermined attenuation factor and the signal value attenuated by the attenuation section 206y by the predetermined attenuation factor (S106).

Next, the defect detecting section 132 sets the first attenuation factor to the predetermined attenuation factor, and sets the second attenuation factor to the other attenuation factor (S108). Then, the attenuation section 206x attenuates the signal indicating the quantity of backscattered electrons detected by the backscattered electron detectors 44xa and 44xb by the predetermined attenuation factor, and the attenuation section 206y attenuates the signal indicating the quantity of backscattered electrons detected by the backscattered electron detectors 44ya and 44yb by the other attenuation factor. Then, the defect detecting section 132 stores the signal value supplied from the adder 208 through the signal processing section 210 in S108, i.e., the second detected signal value which is a summation of the signal value attenuated by the attenuation section 206x by the predetermined attenuation factor and the signal value attenuated by the attenuation section 206y by the other attenuation factor (110).

Next, the defect detecting section 132 sets the first attenuation factor to the other attenuation factor, and sets the second attenuation factor to the predetermined attenuation factor (S112). The attenuation section 206x attenuates the signal indicating the quantity of backscattered electrons detected by the backscattered electron detectors 44xa and 44xb by the other attenuation factor, and the attenuation section 206y attenuates the signal indicating the quantity of backscattered electrons detected by the backscattered electron detectors 44ya and 44yb by the predetermined attenuation factor. Then, the defect detecting section 132 stores the signal value supplied from the adder 208 through the signal processing section 210 in S112, i.e., the third detected signal value which is a summation of the signal value attenuated by the attenuation section 206x by the other attenuation factor and the signal value attenuated by the attenuation section 206y by the predetermined attenuation factor (S114).

Next, the defect detecting section 132 judges whether the difference between the first detected signal value stored in S106 and the ideal value stored on the ideal value storage section 134 is within the permissible value a, stored on the permissible value storage section 136 (S116). In S116, when it is judged that the difference between the first detected signal value and the ideal value is not within the permissible value $\alpha_1$, the defect detecting section 132 detects that at least two of the backscattered electron detectors 44xa, 44xb, 44ya, and 44yb are defective (S118).

In S116, when it is judged that the difference between the first detected signal value and the ideal value is within the permissible value $\alpha_1$, the defect detecting section 132 judges whether each of the difference between the second detected signal value stored in S110 and the half of the first detected signal value, and the difference between the third detected signal value stored in S114 and the half of the first detected signal value, is within the permissible value $\alpha_2$, which is smaller than the permissible value $\alpha_1$ (S120). In S120, when it is measured that each of the difference between the second detected signal value and the half of the first detected signal value, and the difference between the third detected signal value and the half of the first detected signal value, is within the permissible value $\alpha_2$, the defect detecting section 132 detects that the backscattered electron detectors 44xa, 44xb, 44ya, and 44yb are normal (S122). Then, when the defect detecting section 132 detects that the backscattered electron detectors 44xa, 44xb, 44ya, and 44yb are normal, the ideal value storage section 134 stores the first detected signal value stored in S106 as the ideal value (S123).

In S120, when it is measured that each of the difference between the second detected signal value and the half of the first detected signal value, or the difference between the third detected signal value and the half of the first detected signal value, is not within the permissible value $\alpha_2$, the defect detecting section 132 compares the second detected signal value stored in S110 with the third detected signal value stored in S114 (S124). In S124, when it is measured that the second detected signal value is less than the third detected signal value, it is detected that at least one of the backscattered electron detectors 44xa and 44xb is defective (S126). Alternatively, in S124, when it is measured that the second detected signal value is less than the third detected signal value, the defect detecting section 132 detects that at least one of the IV converters 200xa and 200xb, the adder 202x, and the amplifier 204x is defective. In S124, when it is measured that the third detected signal value is less than the second detected signal value, it is detected that at least one of the backscattered electron detectors 44ya and 44yb is defective (S128). Alternatively, in S124, when it is measured that the third detected signal value is less than the second detected signal value, the defect detecting section 132 detects that at least one of the IV converters 200ya and 200yb, the adder 202y, and the amplifier 204y is defective.

According to the electron beam exposure apparatus in the present embodiment, the test for detecting the defect of the backscattered electron detector can be easily performed using software. Therefore, the periodical test can be performed frequently, without stopping operation of the electron beam exposure apparatus. Moreover, even when one of the plurality of backscattered electron detectors is in failure, the defective backscattered electron detector is certainly detectable by adjusting the ideal value and the permissible values. Therefore, the electron beam exposure apparatus can perform the calibration of the irradiation position of the electron beam, the measurement of the pattern width formed on the wafer, etc. accurately using the backscattered electron detectors.

As described above, according to the present invention, there are provided the electron beam irradiation apparatus, the electron beam exposure apparatus, and the defect detection method for easily detecting the defect of the backscattered electron detector.

Although the present invention has been described by way of an exemplary embodiment, it should be understood that those skilled in the art might make many changes and substitutions without departing from the spirit and the scope of the present invention. It is obvious from the definition of the appended claims that embodiments with such modifications also belong to the scope of the present invention.

What is claimed is:

1. An electron beam irradiation apparatus for irradiating an electron beam to an object, comprising:
   an electron beam generating section for generating an electron beam;
   a plurality of backscattered electron detectors for detecting backscattered electrons generated when the electron beam is irradiated on a mark;
   a plurality of attenuation sections for attenuating signal values indicating quantity of backscattered electrons detected by said plurality of backscattered electron detectors; and
   a defect detecting section for detecting a defect of said plurality of backscattered electron detectors based on the signal values attenuated by said plurality of attenuation sections, with attenuation factors for said plurality of attenuation sections being varied.

2. The electron beam irradiation apparatus as claimed in claim 1, further comprising:
   a plurality of IV converters for converting the quantity of electrons detected by said plurality of backscattered electron detectors in to voltages, and for generating signal values indicating the quantity of the backscattered electrons; and
   a plurality of amplifiers for amplifying the signal values generated by said plurality of IV converters, wherein said defect detecting section detects a defect of said plurality of backscattered electron detectors, said plurality of IV converters, and said plurality of amplifiers.

3. The electron beam irradiation apparatus as claimed in claim 1, further comprising an ideal value storage section storing thereon an ideal value, which is a signal value indicating the quantity of the backscattered electrons detected by said plurality of backscattered electron detectors when said plurality of backscattered electron detectors are normal, wherein
   said defect detecting section detects the defect of said plurality of backscattered electron detectors by comparing the signal values attenuated by said plurality of said attenuation sections with the ideal value stored on said ideal value storage section.

4. The electron beam irradiation apparatus as claimed in claim 3, further comprising an attenuated signal adder for adding a signal value attenuated by a first attenuation section of said plurality of attenuation sections, and a signal value attenuated by a second attenuation section of said plurality of attenuation sections, wherein
   said first attenuation section attenuates the signal value indicating the quantity of the backscattered electrons detected by a first backscattered electron detector of said plurality of backscattered electron detectors by a first attenuation factor based on control of said defect detecting section,
   said second attenuation section attenuates the signal value indicating the quantity of the backscattered electrons detected by a second backscattered electron detector of said plurality of backscattered electron detectors by a second attenuation factor based on control of said defect detecting section,
   said attenuated signal adder adds the signal value attenuated by said first attenuation section by the first attenuation factor, and the signal value attenuated by said second attenuation section by the second attenuation factor, and supplies the added signal to said defect detecting section, and said defect detecting section detects the defect of at least one of said first backscattered electron detector and said second backscattered electron detector by varying the first attenuation factor and the second attenuation factor.

5. The electron beam irradiation apparatus as claimed in claim 1, further comprising:
a plurality of detected signal adders for adding signal values indicating the quantity of the backscattered electrons detected by said plurality of backscattered electron detectors; and
an attenuated signal adder for adding a signal value attenuated by a first attenuation section of said plurality of attenuation sections, and a signal value attenuated by a second attenuation section of said plurality of attenuation sections, wherein
said plurality of backscattered electron detectors comprise:
a first backscattered electron detector and a second backscattered electron detector disposed across an optical axis of the electron beam; and
a third backscattered electron detector and a fourth backscattered electron detector disposed across the optical axis of the electron beam,
said plurality of detected signal adders comprise:
a first detected signal adder for adding a signal value indicating the quantity of the backscattered electrons detected by said first backscattered electron detector, and a signal value indicating the quantity of the backscattered electrons detected by said second backscattered electron detector; and
a second detected signal adder for adding a signal value indicating the quantity of the backscattered electrons detected by said third backscattered electron detector, and a signal value indicating the quantity of the backscattered electrons detected by said fourth backscattered electron detector,
said plurality of attenuation sections comprise:
a first attenuation section for attenuating a signal value added by said first detected signal adder by a first attenuation factor; and
a second attenuation section for attenuating a signal value added by said second detected signal adder by a second attenuation factor,
said attenuated signal adder adds the signal value attenuated by said first attenuation section by the first attenuation factor, and the signal value attenuated by said second attenuation section by the second attenuation factor, and supplies the added signal to said defect detecting section, and
said defect detecting section detects defect of at least one of said first backscattered electron detector, said second backscattered electron detector, said third backscattered electron detector, and said fourth backscattered electron detector by varying the first attenuation factor and the second attenuation factor.

6. The electron beam irradiation apparatus as claimed in claim 5, further comprising:
an ideal value storage section storing thereon an ideal value which is a signal value to be supplied from said attenuated signal adder to said defect detecting section when said first backscattered electron detector, said second backscattered electron detector, said third backscattered electron detector, and said fourth backscattered electron detector are normal and when each of the first attenuation factor and the second attenuation factor is set to a predetermined attenuation factor; and a permissible value storage section storing thereon a predetermined permissible value used as a judgment criterion of defect detection, wherein
said defect detecting section judges whether a difference between a first detected signal value, which is a signal value supplied from said attenuated signal adder when each of the first attenuation factor and the second attenuation factor is set to the predetermined attenuation factor, and the ideal value stored on said ideal value storage section is within the predetermined permissible value, and said defect detecting section detects that at least two of said first backscattered electron detector, said second backscattered electron detector, said third backscattered electron detector, and said fourth backscattered electron detector are defective when it is measured that the difference between the first detected signal value and the ideal value is not within the predetermined permissible value.

7. The electron beam irradiation apparatus as claimed in claim 6, wherein
said permissible value storage section further stores another permissible value, which is smaller than the predetermined permissible value,
said defect detecting section judges whether each of a difference between the second detected signal value and the half of the first detected signal value, and a difference between the third detected signal value and the half of the first detected signal value, is within the other permissible value when it is measured that the difference between the first detected signal value and the ideal value is within the predetermined permissible value, and said defect detecting section detects that said first backscattered electron detector, said second backscattered electron detector, said third backscattered electron detector, and said fourth backscattered electron detector are normal when it is judged that each of the difference between the second detected signal value and the half of the first detected signal value, and the difference between the third detected signal value and the half of the first detected signal value, is within the other permissible value, where
the second detected signal value is a signal value supplied from said attenuated signal adder when the first attenuation factor is set to the predetermined attenuation factor and the second attenuation factor is set to another attenuation factor, which is greater than the predetermined attenuation factor, and
the third detected signal value is a signal value supplied from said attenuated signal adder when the first attenuation factor is set to the other attenuation factor and the second attenuation factor is set to the predetermined attenuation factor.

8. The electron beam irradiation apparatus as claimed in claim 7, wherein said defect detecting section compares the second detected signal value with the third detected signal value when it is measured that either the difference between the second detected signal value and the half of the first detected signal value, or the difference between the third detected signal value and the half of the first detected signal value, is not within the other permissible value, and said defect detecting section detects that at least one of the first backscattered electron detector and the second backscattered electron detectors is defective when the second detected signal value is less than the third detected signal value, and said defect detecting section detects that at least one of the third backscattered electron detector or the fourth backscattered electron detectors is defective when the third detected signal value is less than the second detected signal value.

9. A defect detection method of detecting a defect of a backscattered electron detector, comprising steps of:
   detecting backscattered electrons by a plurality of backscattered electron detectors, the backscattered electrons being generated when an electron beam is irradiated on the mark;
   attenuating signal values indicating quantity of backscattered electrons detected by the plurality of backscattered electron detectors; and
   detecting a defect of the plurality of backscattered electron detectors based on attenuated signal values, with attenuation factors in said attenuation step being varied.

10. The defect detection method as claimed in claim 9, wherein said defect detection step comprises a step of detecting defect of the plurality of backscattered electron detectors by comparing the ideal value, which is a signal value indicating the quantity of the backscattered electrons detected by the plurality of backscattered electron detectors when the plurality of backscattered electron detectors are normal, with the signal value attenuated in said attenuation step.

11. The defect detection method as claimed in claim 9, wherein said attenuation step comprises steps of:
   attenuating a signal value indicating the quantity of the backscattered electrons detected by a first backscattered electron detector of the plurality of backscattered electron detectors by a first attenuation factor; and
   attenuating a signal value indicating the quantity of the backscattered electrons detected by a second backscattered electron detector of the plurality of backscattered electron detectors by a second attenuation factor, wherein
      a defect of at least one of the first backscattered electron detector and the second backscattered electron detector is detected in said defect detection step based on a signal value, which is a summation of the signal value attenuated by the first attenuation factor and the signal value attenuated by the second attenuation factor in said attenuation steps by varying the first attenuation factor and the second attenuation factor.

12. The defect detection method as claimed in claim 9, wherein
   said backscattered electron detection step comprises a step of detecting the backscattered electrons by a first backscattered electron detector and a second backscattered electron detector disposed across an optical axis of the electron beam, and by a third backscattered electron detector and a fourth backscattered electron detector disposed across an optical axis of the electron beam,
   said attenuation step comprises steps of:
      generating a first attenuation signal value by attenuating the signal value, which is a summation of the signal value indicating the quantity of backscattered electrons detected by the first backscattered electron detector and the signal value indicating the quantity of backscattered electrons detected by the second backscattered electron detector, by a first attenuation factor; and
      generating a second attenuation signal value by attenuating the signal value, which is a summation of the signal value indicating the quantity of backscattered electrons detected by the third backscattered electron detector and the signal value indicating the quantity of backscattered electrons detected by the fourth backscattered electron detector, by a second attenuation factor, and
   a defect of at least one of the first backscattered electron detector, the second backscattered electron detector, the third backscattered electron detector, and the fourth backscattered electron detector is detected in said defect detection step based on the signal value, which is a summation of the first attenuation signal value and the second attenuation signal value generated in said attenuation step, by varying the first attenuation factor and the second attenuation factor.

13. The defect detection method as claimed in claim 12, wherein said defect detection step comprises steps of:
   judging whether difference between a first detected signal value and an ideal value is within a predetermined permissible value; and
   detecting that at least two of the first backscattered electron detector, the second backscattered electron detector, the third backscattered electron detector, and the fourth backscattered electron detectors are defective when it is measured that the difference between the first detected signal value and the ideal value is not within the predetermined permissible value, where
      the first detected signal value is a summation of the first attenuation signal value and the second attenuation signal value where each of the first attenuation factor and the second attenuation factor is set to a predetermined attenuation factor, and
      the ideal value is a summation of the first attenuation signal value and the second attenuation signal value when the first backscattered electron detector, the second backscattered electron detector, the third backscattered electron detector, and the fourth backscattered electron detector are normal and each of the first attenuation factor and the second attenuation factor is set to the predetermined attenuation factor.

14. The defect detection method as claimed in claim 13, wherein said defect detection step comprises steps of:
   judging whether each of a difference between a second detected signal value and the half of the first detected signal value, and a difference between a third detected signal value and the half of the first detected signal value, is within another permissible value, which is smaller than the predetermined permissible value, when it is measured that the difference between the first detected signal value and the ideal value is within the predetermined permissible value; and
   detecting that the first backscattered electron detector, the second backscattered electron detector, the third backscattered electron detector, and the fourth backscattered electron detector are normal when it is judged that each of the difference between the second detected signal value and the half of the first detected signal value, and the difference between the third detected signal value and the half of the first detected signal value, is within the other permissible value, where
      the second detected signal value is a summation of the first attenuation signal value and the second attenuation signal value when the first attenuation factor is set to the predetermined attenuation factor and the second attenuation factor is set to another attenuation factor, which is greater than the predetermined attenuation factor, and
      the third detected signal is a summation of the first attenuation signal value and the second attenuation signal value when the first attenuation factor is set to the other attenuation factor and the second attenuation factor is set to the predetermined attenuation factor.

15. The defect detection method as claimed in claim 14, further comprising a step of storing the first detected signal value as the ideal value when it is detected in said defect detection step that the first backscattered electron detector, the second backscattered electron detector, the third backscattered electron detector, and the fourth backscattered electron detector are normal.

16. The defect detection method as claimed in claim 14, wherein said defect detection step comprises steps of:

comparing the second detected signal value with the third detected signal value when at least either the difference between the second detected signal value and the half of the first detected signal value, or the difference between the third detected signal value and the half of the first detected signal value, is not within the other permissible value; and detecting that at least one of the first backscattered electron detector and the second backscattered electron detector is defective when the second detected signal value is less than the third detected signal value, and detecting that at least one of the third backscattered electron detector and the fourth backscattered electron detector is defective when the third detected signal value is less than the second detected signal value.

17. An electron beam exposure apparatus for exposing a pattern on a wafer by an electron beam, comprising:

an electron beam generating section for generating an electron beam;

a plurality of backscattered electron detectors for detecting backscattered electrons generated when the electron beam is irradiated on a mark;

a plurality of attenuation sections for attenuating signal values indicating quantity of backscattered electrons detected by said plurality of backscattered electron detectors; and a defect detecting section for detecting a defect of said plurality of backscattered electron detectors by varying attenuation factors for said plurality of attenuation sections.

* * * * *